US008005686B2

(12) United States Patent
Smith

(10) Patent No.: US 8,005,686 B2
(45) Date of Patent: Aug. 23, 2011

(54) INTEGRATED POINT-OF-CARE SYSTEMS AND METHODS

(76) Inventor: Baird M. Smith, Monte Sereno, CA (US)

( * ) Notice: Subject to any disclaimer, the term of this patent is extended or adjusted under 35 U.S.C. 154(b) by 1307 days.

(21) Appl. No.: 10/825,729

(22) Filed: Apr. 16, 2004

(65) Prior Publication Data

US 2004/0249673 A1    Dec. 9, 2004

Related U.S. Application Data

(60) Provisional application No. 60/463,999, filed on Apr. 18, 2003.

(51) Int. Cl.
*G06Q 10/00* (2006.01)
(52) U.S. Cl. .............................. 705/2; 705/3
(58) Field of Classification Search ............ 705/2, 3
See application file for complete search history.

(56) References Cited

U.S. PATENT DOCUMENTS

| | | | |
|---|---|---|---|
| 4,347,851 A | 9/1982 | Jundanian | |
| 4,633,237 A | 12/1986 | Tucknott et al. | |
| 4,768,241 A | 9/1988 | Beney | |
| 4,803,625 A | 2/1989 | Fu et al. | |
| 5,253,656 A | 10/1993 | Rincoe et al. | |
| 5,335,651 A | 8/1994 | Foster et al. | |
| 5,343,869 A | 9/1994 | Pross et al. | |
| 5,417,222 A | 5/1995 | Dempsey et al. | |
| 5,455,975 A | 10/1995 | Foster | |
| 5,497,766 A | 3/1996 | Foster et al. | |
| 5,664,270 A | 9/1997 | Bell et al. | |
| 5,678,562 A | 10/1997 | Sellers | |
| 5,687,717 A | 11/1997 | Halpern et al. | |
| 5,749,374 A | 5/1998 | Schneider, Sr. | |
| 5,993,400 A | 11/1999 | Rincoe et al. | |
| 6,017,307 A | 1/2000 | Raines | |
| 6,111,509 A | 8/2000 | Holmes | |
| 6,139,494 A * | 10/2000 | Cairnes | 600/300 |
| 6,149,587 A | 11/2000 | Raines | |
| 6,162,180 A | 12/2000 | Miesel et al. | |
| 6,168,563 B1 | 1/2001 | Brown | |
| 6,171,237 B1 | 1/2001 | Avitall et al. | |
| 6,205,601 B1 * | 3/2001 | Nessmann et al. | 5/600 |
| 6,206,837 B1 | 3/2001 | Brugnoli | |
| 6,234,172 B1 | 5/2001 | Ausbourne et al. | |
| 6,264,614 B1 | 7/2001 | Albert et al. | |
| 6,360,389 B1 | 3/2002 | Gallant et al. | |
| 6,362,725 B1 | 3/2002 | Ulrich et al. | |

(Continued)

OTHER PUBLICATIONS

"'Smart' Hospital to Improve Care," BBCNews, May 7, 2003, located at http://news.bbc.co.uk/2/hi/technology/3004089.stm.

(Continued)

*Primary Examiner* — Lena Najarian
(74) *Attorney, Agent, or Firm* — Carr & Ferrell LLP

(57) ABSTRACT

An integrated point-of-care system includes a medical monitoring device, a medical care device, a computing system, and a structure. The medical monitoring device monitors patient information for a patient. The medical care device provides medical care to the patient. The computing system receives patient information from the medical monitoring device and transmits control instructions to the medical care device to control the medical care to the patient. The computing system also exchanges data with a central data respository through a communication network. The structure supports the patient, the medical monitoring device, the medical care device, and the computing system. The structure can also transport the patient, the medical monitoring device, the medical care device, and the computing system together.

26 Claims, 9 Drawing Sheets

U.S. PATENT DOCUMENTS

| | | | |
|---|---|---|---|
| 6,421,650 B1 | 7/2002 | Goetz et al. | |
| 6,441,742 B1 | 8/2002 | Lovely et al. | |
| 6,485,441 B2 | 11/2002 | Woodward | |
| 6,493,568 B1 | 12/2002 | Bell et al. | |
| 6,671,563 B1 | 12/2003 | Engelson et al. | |
| 6,681,003 B2 | 1/2004 | Linder et al. | |
| 6,685,633 B2 | 2/2004 | Albert et al. | |
| 6,876,303 B2* | 4/2005 | Reeder et al. | 340/573.1 |
| 2001/0056226 A1 | 12/2001 | Zodnik et al. | |
| 2002/0014951 A1 | 2/2002 | Kramer et al. | |
| 2002/0044043 A1 | 4/2002 | Chaco et al. | |
| 2002/0044059 A1 | 4/2002 | Reeder et al. | |
| 2002/0047075 A1* | 4/2002 | Metz et al. | 248/229.1 |
| 2002/0103674 A1 | 8/2002 | Reeder et al. | |
| 2002/0186136 A1 | 12/2002 | Schuman | |
| 2003/0010345 A1 | 1/2003 | Koblasz et al. | |
| 2003/0037375 A1 | 2/2003 | Riley et al. | |
| 2003/0050539 A1 | 3/2003 | Naghavi et al. | |
| 2003/0052787 A1 | 3/2003 | Zerhusen et al. | |
| 2003/0140928 A1 | 7/2003 | Bui et al. | |
| 2003/0163348 A1* | 8/2003 | Stead et al. | 705/2 |

OTHER PUBLICATIONS

"Instrumentarium's Ohmeda Medical Division Introduces the Giraffe(TM) OmniBed(TM) at the World Congress on Pediatric Intensive Care," PR Newswire, Jun. 25, 2000, located at http://www.findarticles.com/cf_dls/m4PRN/2000_June_2/62908511/print.jhtml.

Giraffe(TM) OmniBed(TM) Product Specifications, Ohmeda Medical, date unknown.

Giraffe(TM) OmniBed(TM) Operator's Manual, Ohmeda Medical, Aug. 8, 2001.

* cited by examiner

INTEGRATED POINT-OF-CARE SYSTEMS AND METHODS

CROSS-REFERENCE TO RELATED APPLICATIONS

The application claims the benefit of U.S. Provisional Application No. 60/463,999 filed on Apr. 18, 2003 and entitled "Medical Interactive Bed System", which is hereby incorporated by reference.

BACKGROUND

1. Field of the Invention

The present invention relates generally to medical devices and techniques, and more particularly to integrated point-of-care systems and methods for providing medical care to a patient.

2. Background Art

In modern medical health care facilities (i.e. doctors' offices, skilled nursing facilities, chronic care facilities, home care facilities, and hospitals), health care personnel use various medical devices to view patient information or provide medical care to a patient. Some medical care devices administer medical care—for example, an intravenous pump that delivers a solution containing a medication into a patient's bloodstream or a ventilator that delivers oxygen to a patient's lungs. Other medical monitoring devices measure and report a patient's physiological status—for example, an electrocardiograph (EKG) that measures and records electrical currents associated with heart contractions or a sphygmomanometer that measures blood pressure.

Typically, the patient is lying in a bed surrounded by various medical devices. In some cases, the medical devices are awkwardly and dangerously arranged around the patient's bed. The medical devices may hang from the ceiling, hang from bed rails, lie on the bed, sit on the floor, or sit on dedicated pedestals. The placement of these medical devices is often random and creates serious safety risks to the patient. There are also risks to health care personnel who attempt to carry or maneuver heavy devices in crowded quarters. Additionally, these medical devices have cords, wires, and tubes arranged in a tangled web that poses a safety risk. Also, many medical devices have their own display panel and control panel, which may be small (difficult to see), awkwardly located, space occupying, expensive, and redundant. Many medical devices include their own battery, which in addition to the extra control panels and read-out screens, takes up space and adds weight and expense. In certain rooms such as an intensive care unit, efficient organization of medical devices and utilization of space are even more critical due to the unstable, critical condition of the patient, number of devices, and the high cost of space.

In some circumstances, it may be necessary to transport medical devices along with a patient in order to sustain medical care during transport. In some prior art solutions, the medical devices are transported in a structure specifically designed for the medical devices, alongside, behind, in front of, or under the patient. This can be difficult and dangerous when passing through narrow spaces such as a crowded ward, doorway, or elevator. Also, separate structures for the medical devices require more medical personnel to transport the patient.

The nonstandard wires, tubes, and interfaces of the medical devices also pose a health and safety hazard to the patient and/or health care personnel during transport of the patient. Specifically, the medical devices may need to be detached from the patient and/or other medical devices prior to transport. Upon arrival at a different location, similar medical devices may need to be reattached. The processes of detaching and reattaching the medical devices to the patient are problematic for the health care personnel. Additionally, the array of wires, tubes, and interfaces may inadvertently detach from the patient or from each other during transport. Moreover, the medical devices may need to be connected to a portable power source during transport. Furthermore, the data generated by these devices is usually lost during transport as currently there is no one to transcribe it onto paper or input into the hospital's central data repository. A heavy device may fall during transport, jeopardizing the device, anyone in the way, and the back of anyone who tries to catch it.

Generally, the various medical devices surrounding a patient's bed operate independently of each other and include non-standard wires, tubes, and interfaces. One problem is lack of integration between the medical devices. For example, some medical devices generate information in a proprietary format, which is not compatible with other medical devices from different vendors. In another example, a medical device may produce an analog signal for a patient's vital signs. Because the signal is not digital or recorded, the analog signal must be transcribed onto a piece of paper or else the information is lost. As a result of this lack of integration, health care personnel must pay greater attention to control and monitor many medical devices individually—requiring more personnel to transcribe the data, more time to review the data, and greater potential for lost data and transcription error. Some devices with analog signals may store the data for short periods of time but again, the time must be taken later to review and transcribe the information.

Additionally, many medical devices operate independent of a health care computer system or an electronic medical record (EMR) in which a database of patient medical records is stored. Consequently, health care personnel need to read information from the medical devices and manually enter the information into the health care computer system for storage in the database. In one example, data from medical devices such as glucometers, EKG apparatuses, intravenous (IV) pumps, blood pressure monitoring, ventilators, and respiratory devices are not linked to the EMR. Manual transfer of information from the medical devices to the health care computer system is time-consuming and prone to error.

The aforementioned problems and inefficiencies with medical devices are of particular concern in intensive care units for neonates, children, and adults. In these environments, the patients are sicker; consequently, there is a greater volume of information per patient. Therefore, there is an even greater need to have an efficient point-of-care system to integrate, display, and control medical devices.

Current methods for communicating information about a patient often involves paper which can be lost or difficult to access, particularly when this information may be generated in different parts of a medical care facility but still pertains to the same patient. For example, there may be information from a blood-testing laboratory, a radiology facility, a specialist's visit, a nursing assessment, and an operating room or procedural facility. It is also not searchable electronically nor easily graphed—the comparison of current and prior data requires a lengthy search through multiple sheets of paper for comparison.

Verbal and hand-written orders are prone to error, due to confusion about what was said, difficulty interpreting handwriting, and multiple manual steps required to translate the idea into action. Point of care devices and systems used to replace them tend to be time-consuming because of unwieldy software, the small screen geography offered by many devices, and a lack of decision support.

Avoidance of adverse drug events and enhancement of decision-making is best provided at the point of care by devices and systems which can interact patient—specifically with the pharmacy, EMR, laboratory, picture archiving and communication system (PACS) and devices which measure important patient parameters, such as weight, blood pressure, pulse or respiratory rate. This includes the ability to read barcodes, passwords, magnetic badges, and other biometric or radiofrequency information about patients, health providers, and medications.

As some health facilities close and others become busier, facility administrators need better real-time information on bed-use to safely and efficiently run at higher rates of bed utilization. Currently this information is obtained by phone calls, estimates, and verbal reports of bed occupancy and anticipated discharges. It is therefore inaccurate, awkward to collect, and usually late. Also, medical facility administrators do not have an accurate tally of the number of devices used by an individual patient (therefore they can not charge for them), or the number of devices used aggregately by all their patients, or the devices which are unused on one floor but may be needed on another. If a device breaks or malfunctions, it may be complicated to remove and replace it because of the snarl of tubes and wires in which the device may be entrapped.

Insurance agencies would prefer better information on the care of their patients—and some of this information is not currently collected. These agencies would like to define the variables they believe determine quality of care and ask health facilities to report them. These agencies would like real-time information about patient care in order to approve or deny treatment in a timely manner and to know their expenses. The insurance agencies would also like real-time information provided in digital format in order to streamline and diminish the cost of billings and collections.

One prior solution for neonatal care is Ohmeda Medical Division's Giraffe™ OmniBed™. The OmniBed is a neonatal care station that includes a warmer and incubator in a mobile environment. The OmniBed converts between a closed incubator and an open bed, thus reducing the need to move the infant from one type of bed to another and facilitating transport.

The approach of some is to display patient information at towers or stands or nursing stations or consoles near a bed, or sliding devices that attach to the bed. These methods have significant degrees of ambiguity and carry the risk that information or orders intended for one patient are applied to another patient nearby because the device is not unambiguously specific to (and cognizant of) one patient.

While prior approaches to improving patient care have had limited success in some circumstances, further improvement is needed in light of the aforementioned problems and inefficiencies with point-of-care medical devices. In particular, there exists a need to integrate point-of-care medical devices and to facilitate transport of the medical devices along with a patient.

SUMMARY OF THE INVENTION

The present invention addresses the need to integrate medical devices, enhance provider decision making, prevent error, and facilitate transport of the medical devices along with a patient. An integrated point-of-care system includes a medical monitoring device, a medical care device, a computing system, and a structure. The medical monitoring device monitors patient information for a patient. The medical care device provides medical care to the patient. The computing system receives patient information from the medical monitoring device and transmits control instructions to the medical care device to control the medical care to the patient. The computing system also exchanges data with a central data repository through a communication network. The structure supports the patient, the medical monitoring device, the medical care device, and the computing system. The structure can also transport the patient, the medical monitoring device, the medical care device, and the computing system together.

The integrated point-of-care system may include an identification device for identifying the patient, persons, or medications. For example, the identification device may be a barcode reader device, fingerprint recognition device, voice recognition device, magnetic strip reader device, radiofrequency chip, or visual recognition device. Additionally, the integrated point-of-care system may include an electronic camera to generate and transmit visual images. For example, the electronic camera may generate visual images of a person so that the identification device can identify the person, or the digital camera may generate visual images of the patient for display at a remote location to a family or consulting specialists.

The integrated point-of-care system may include a display for displaying the data as images for health provides, a Web browser for patient use, a television program, movie, and health information in digitized format (DVD, CD, health card, or other). Additionally, the display may display the patient information, control instructions, and the patient medical records accessed from the health care computing system. Additionally, the integrated point-of-care device may include a portable power supply, such as a battery, to power the computer system and medical devices.

A medical interactive bed system is described herein. The medical interactive bed system gathers vital patient information using sensors, automatically facilitates the entry of patient information into an electronic medical record (EMR), and displays the patient information. The patient information may be gathered in digital form and displayed in a manner that is easy to interpret, manipulate, record and transfer.

By implementing the medical interactive bed system, a whole range of medical devices used in hospitals can be incorporated into an interconnected framework that may reduce the probability of treatment and/or administrative errors, facilitate the use of evidence-based treatment guidelines, and provide an electronic information hub to promote coordination and communication among health providers, patients, and payers. The medical interactive bed system also reduces the space required in a hospital room for medical devices.

The bed system can include a mattress (bed), a mattress support, a set of bed rails, a display screen, a keyboard, a radiant warmer, a vertical frame, intravenous (IV) hooks, medical device storage, and a bed dolly with wheels. The mattress is supported by the mattress support. The mattress may be constructed of a soft material, while the mattress support is a hard structure (plastic or metal). The set of bed rails can be placed in an up position, to prevent a patient from falling out of or leaving the bed, or in a down position to allow patient exit or examination by doctors, nurses, or other health care personnel (health care personnel). At its bottom, the medical interactive bed system is supported by the dolly and can be rolled on the attached wheels. The invention pertains to beds for neonates, children and adults.

Figure 7:
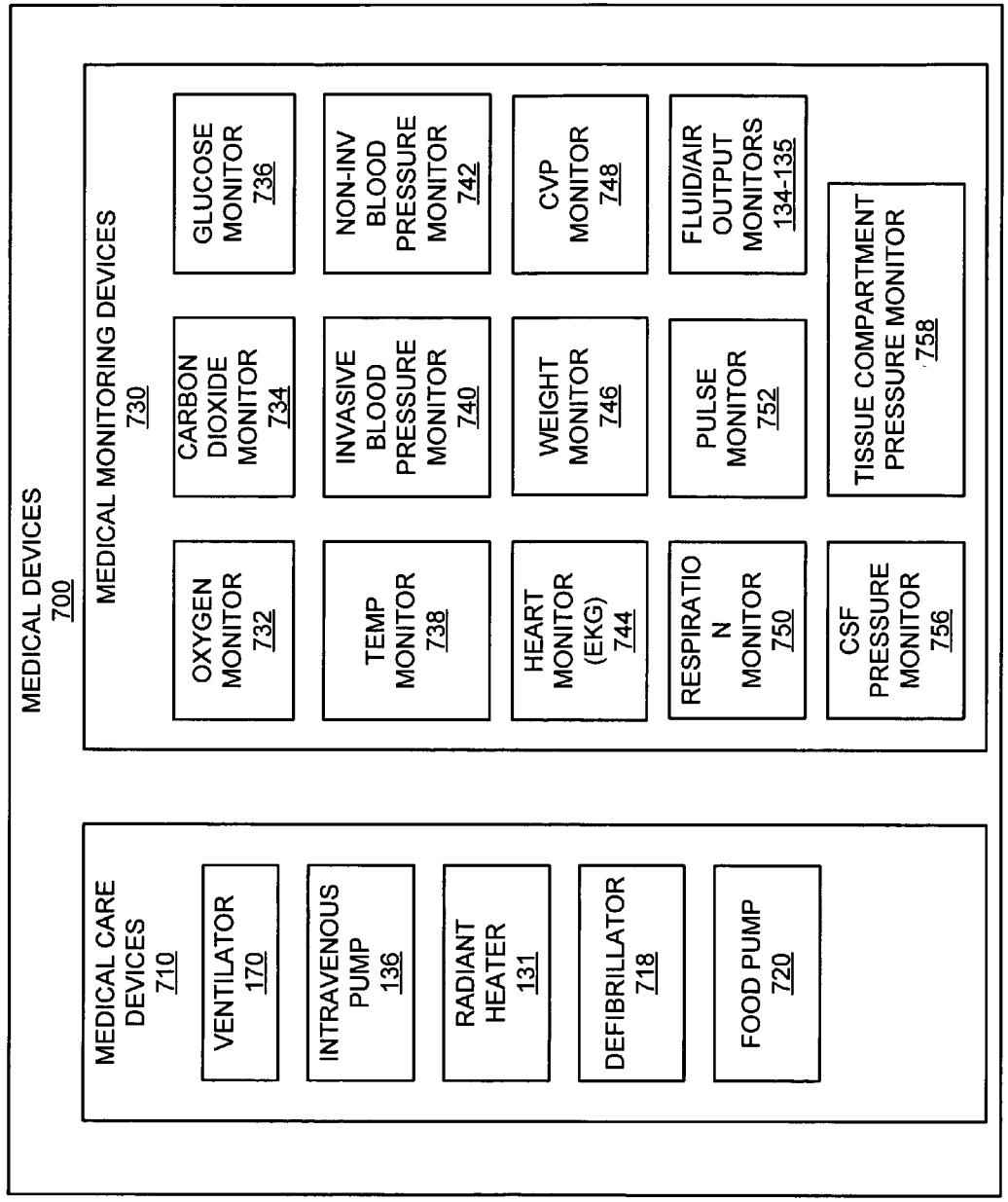
Figure 8:
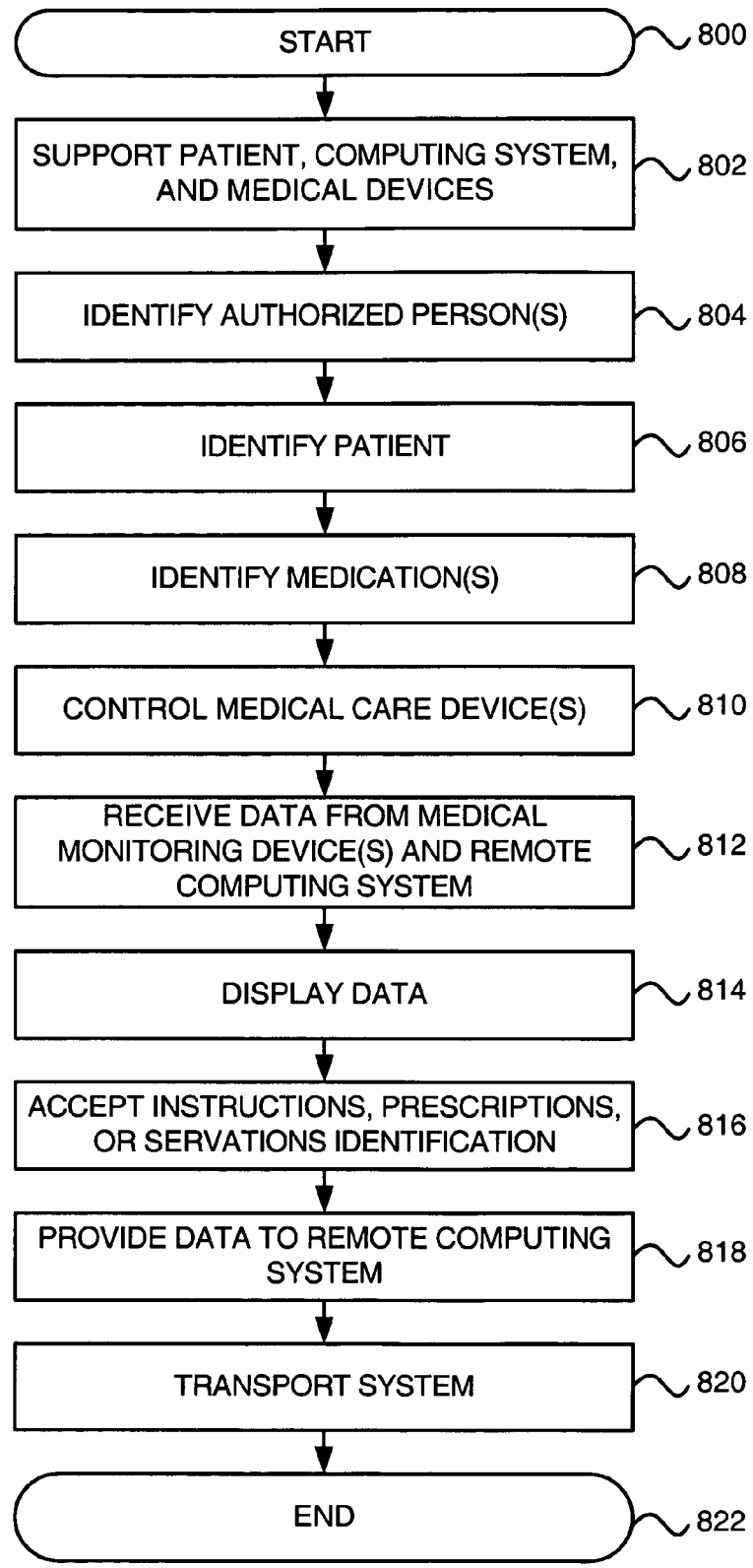
Figure 9:
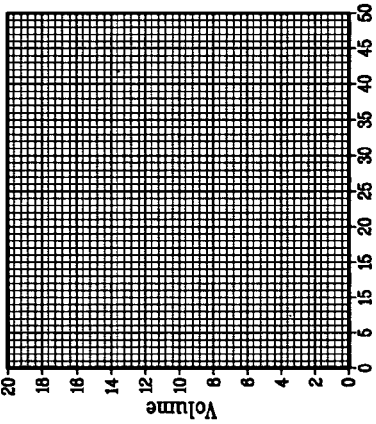

FIG. 7 is a block diagram of exemplary medical devices in an exemplary implementation of the present invention;

FIG. 8 is a flow chart of an exemplary method of operating the patient point-of-care system in an exemplary implementation of the present invention; and FIG. 9 is an exemplary screen shot of a display generated by a graphical user interface in an exemplary implementation of the present invention.

DETAILED DESCRIPTION OF THE INVENTION

The present invention provides an integrated point-of-care system and method for integrating point-of-care medical devices and facilitating transport of the medical devices along with the patient.

An integrated point-of-care system includes a medical monitoring device, a medical care device, a computing system, and a structure. The medical monitoring device monitors patient information for a patient. The medical care device provides medical care to the patient. The computing system receives patient information from the medical monitoring device and transmits control instructions to the medical care device to control the medical care to the patient. The computing system also exchanges data with a central data repository through a communication network. The structure supports the patient, the medical monitoring device, the medical care device, and the computing system. The structure can also transport the patient, the medical monitoring device, the medical care device, and the computing system together.

FIGS. 1-4 depict one embodiment for a patient point-of-care system for a neo-natal care environment. Other embodiments for the patient point-of-care system can be for patients of all ages and illness severity and health care environments such as hospitals, home care, chronic care, wards, intensive care units and military facilities. The embodiments discussed herein are illustrative of one example of the present invention. As these embodiments of the present invention are described with reference to illustrations, various modifications or adaptations of the methods and/or specific structures described may become apparent to those skilled in the art. All such modifications, adaptations, or variations that rely upon the teachings of the present invention, and through which these teachings have advanced the art, are considered to be within the spirit and scope of the present invention. Hence, these descriptions and drawings should not be considered in a limiting sense, as it is understood that the present invention is in no way limited to only the embodiments illustrated.

Figure 1:
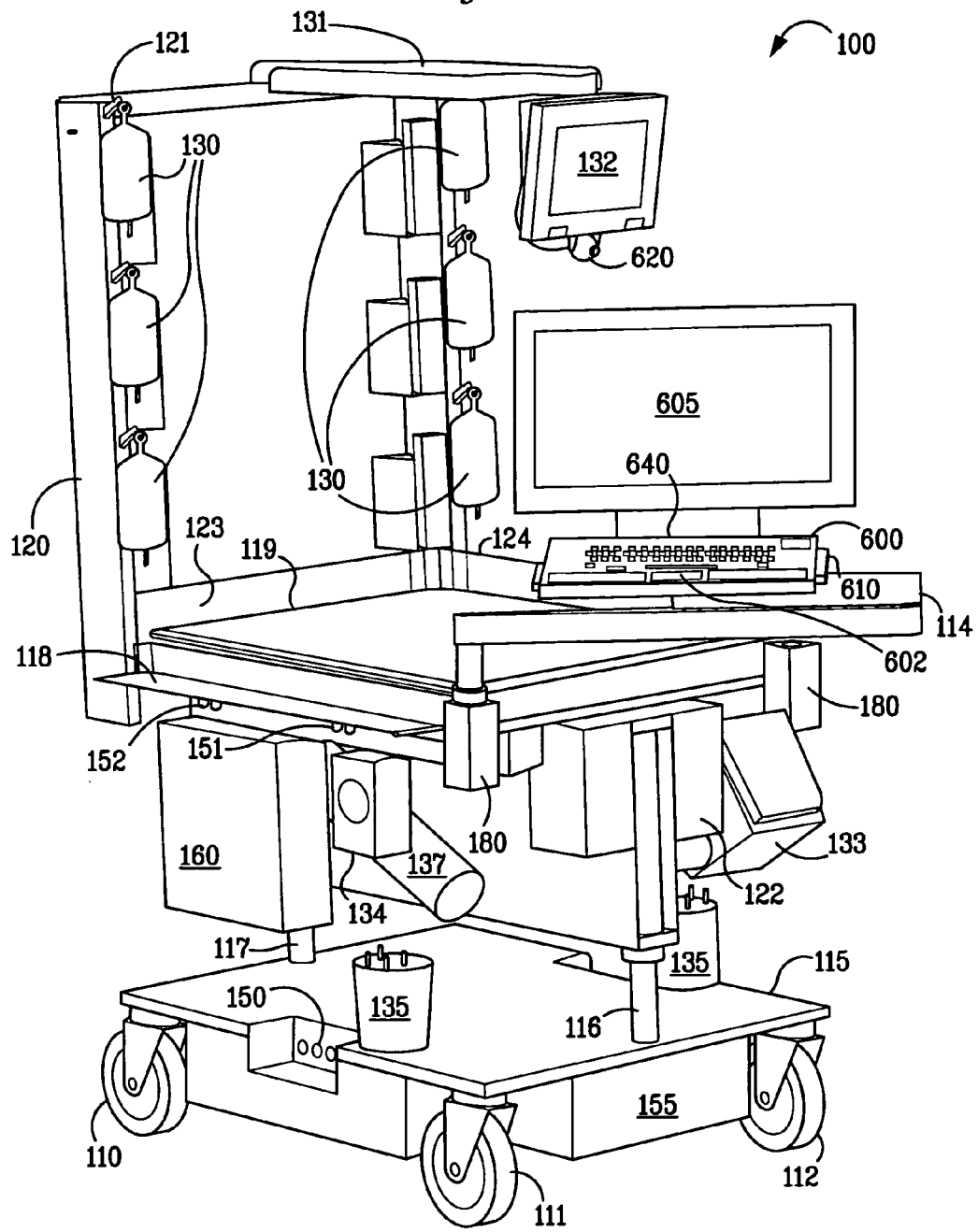
FIG. 1 is a front perspective of a patient point-of-care system in an exemplary implementation of the present invention.
Figure 2:
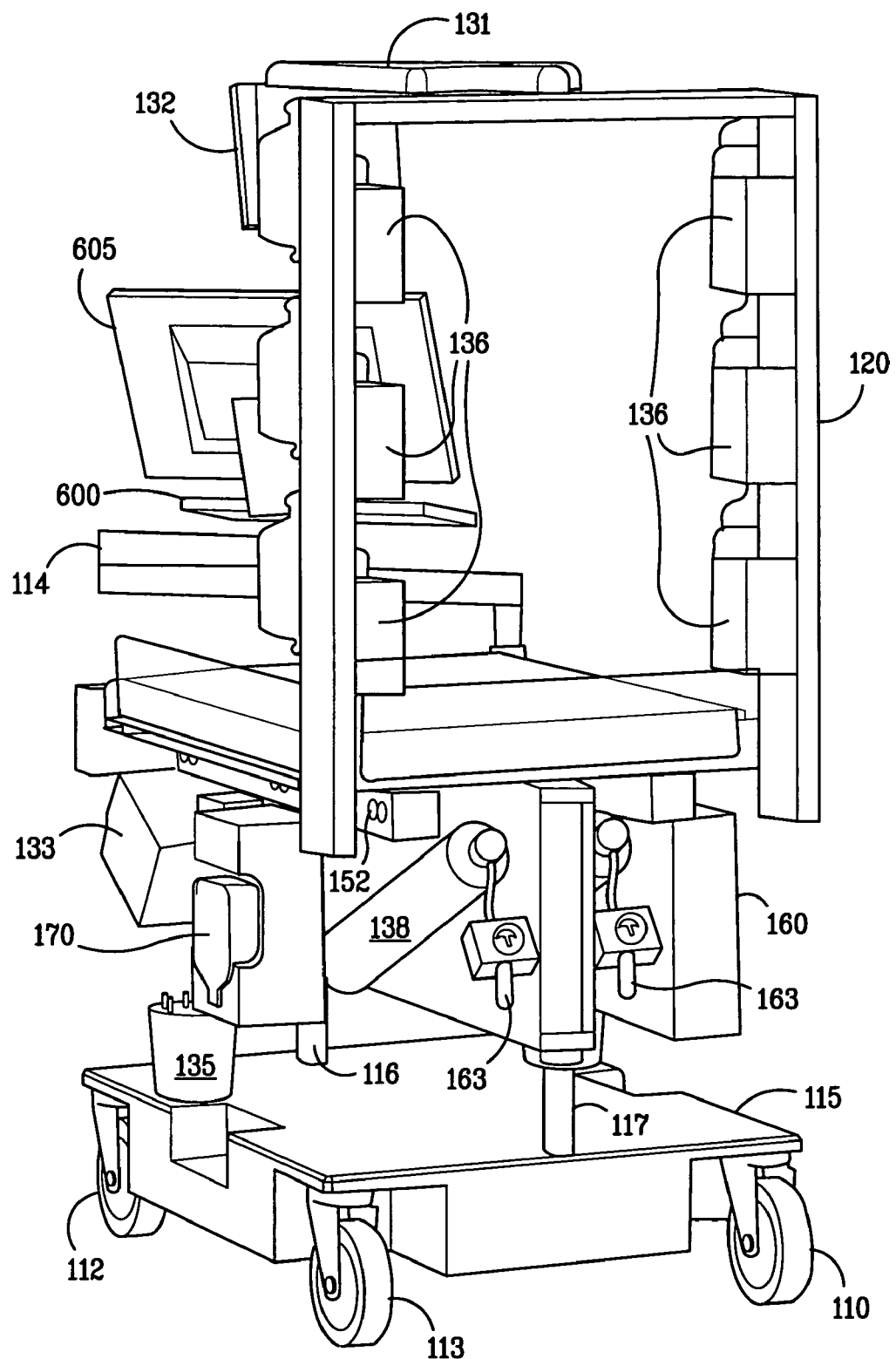
FIG. 2 is a rear perspective of the patient point-of-care system in an exemplary implementation of the present invention.
Figure 3:
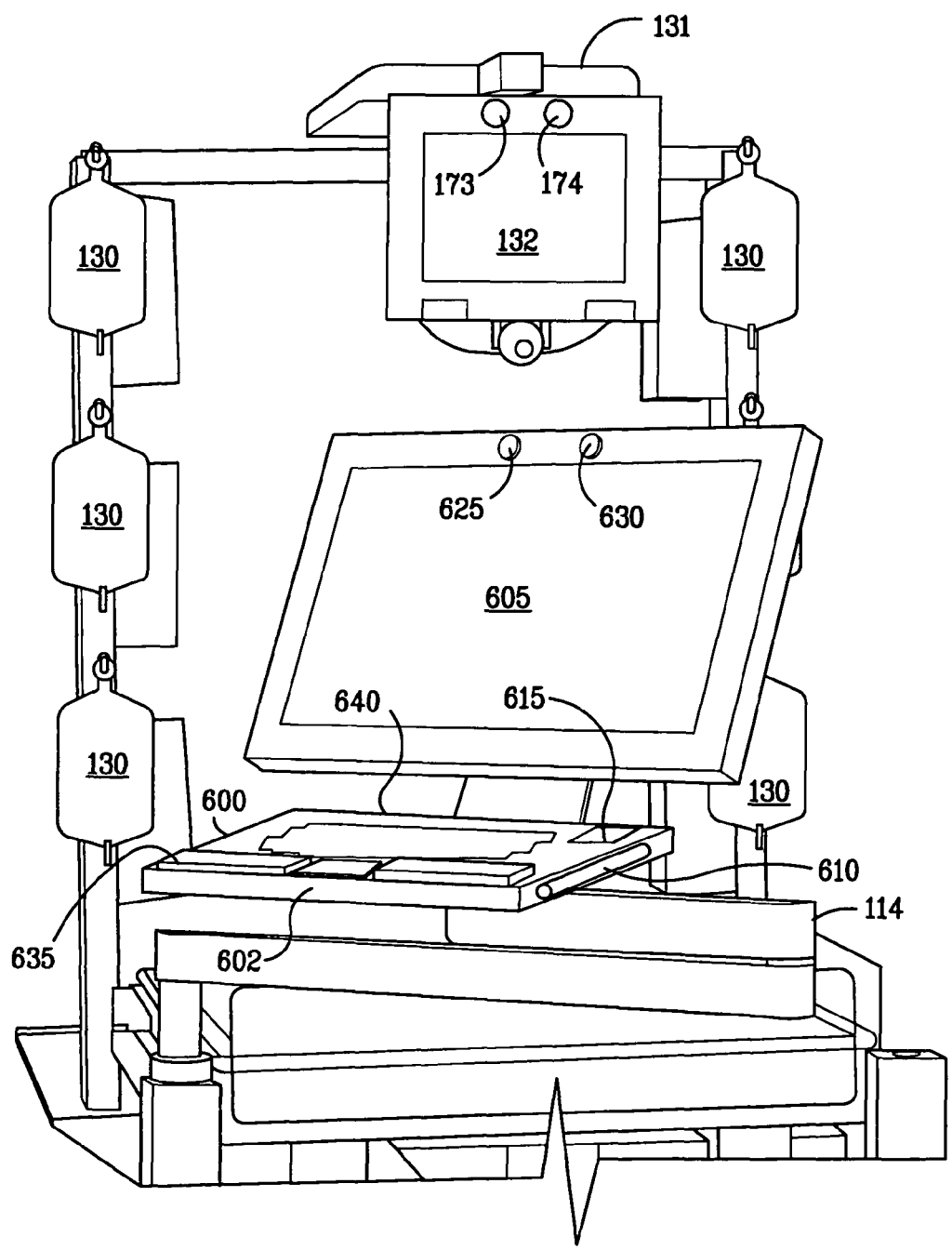
FIG. 3 is a close-up, front perspective of the patient point-of-care system in an exemplary implementation of the present invention.
Figure 4:
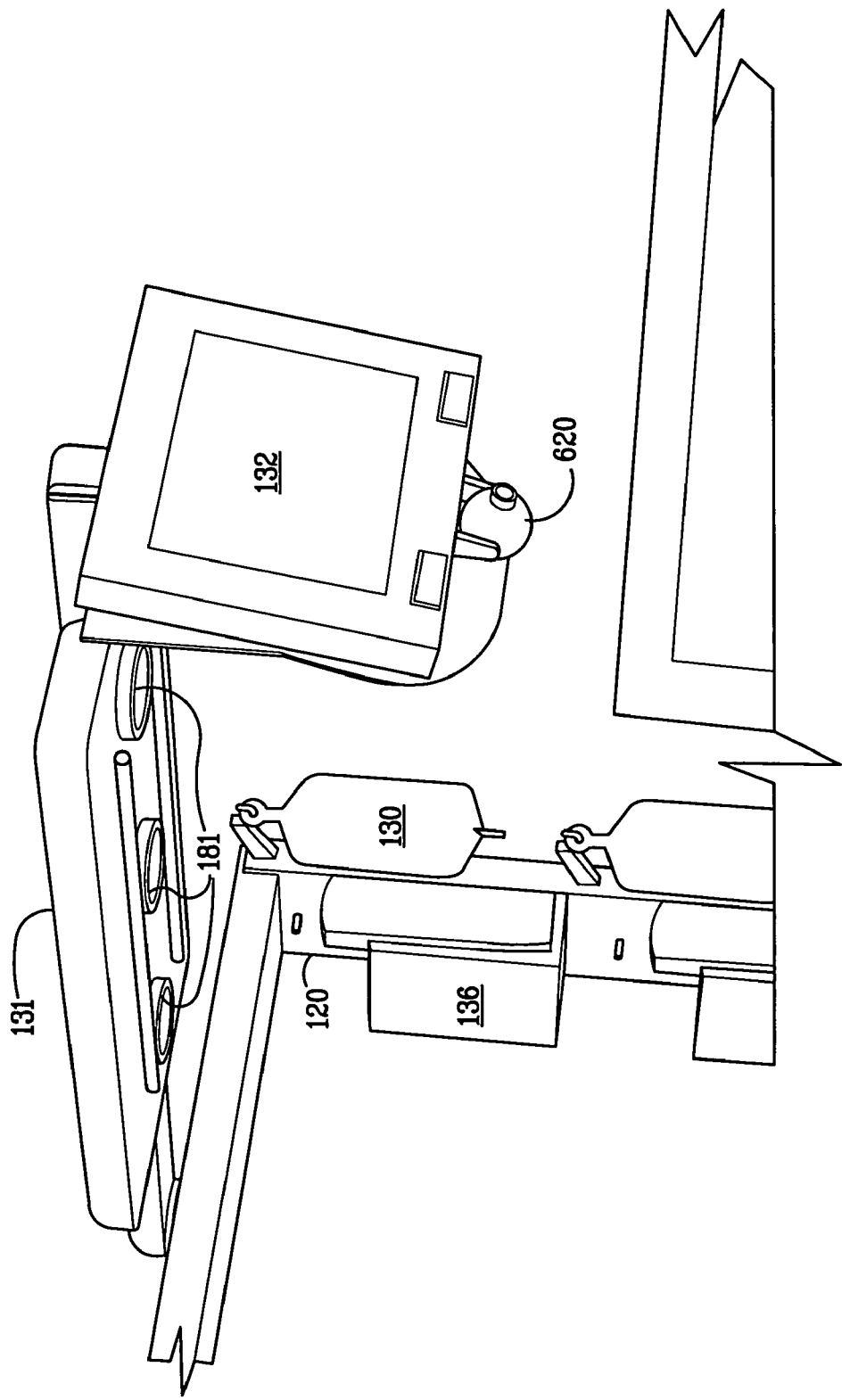
FIG. 4 is a close-up perspective of the top of the patient point-of-care system in an exemplary implementation of the present invention.

FIG. 1 depicts a front perspective of a patient point-of-care system 100 in an exemplary implementation of the present invention. FIG. 2 depicts a rear perspective of a patient point-of-care system 100 in an exemplary implementation of the present invention. FIG. 3 depicts a close-up, front perspective of the patient point-of-care system 100 in an exemplary implementation of the present invention. FIG. 4 depicts a close-up perspective of the top of the patient point-of-care system 100 in an exemplary implementation of the present invention.

The system 100 includes a computing system 160, a structure, and medical devices. A structure is any apparatus configured to support a patient (not shown), a computing system 160, a medical monitoring device, and the medical care device and transport the patient, the computing system 160, the medical monitoring device, and the medical care device together. In this embodiment in FIGS. 1-4, the structure includes a vertical frame 120, a mattress support 118, a mattress 119, a dolly 115, and wheels 110-113. One example of a structure is a bed for a patient.

The computing system 160 is electronically coupled to, and communicates with, one or more medical devices, as is described more fully herein. In some embodiments, the communication between the computing system 160 and the medical devices is wired or wireless such as in the 802.11B, 802.11G, or Bluetooth format. In other embodiments, the computing system 160 and the medical devices include radiofrequency devices for patient recognition, patient location within a hospital, and recognition of health care personnel or medical devices.

The structure supports a patient (not shown), the computing system 105, and the medical devices. Other embodiments for the medical devices are discussed below in FIG. 7. The medical devices provide medical care to the patient and/or monitor the physiological status (e.g., physical condition) of the patient, as is described more fully herein. In this embodiment, the medical devices comprises intravenous pumps 136, intravenous bags 130, a master IV pump control 133, a radiant heater 131, a ventilator 170, fluid/air containers 134-135, and a defibrillator (not shown). The intravenous pumps 136 and the intravenous bags 130 deliver medicated solutions to the patient. The radiant heater 131 warms the patient. The defibrillator is available to interpret the EKG tracing of patients and cardiovert or defibrillate selected patients when appropriate. In this embodiment, the patient is an infant.

In some embodiments, the computing system 160 and medical devices are mounted on the structure for stability. It is to be appreciated that the system 100 facilitates transport of the patient, along with the computing system 160 and the medical devices, as a single unit. This will allow for an efficient transfer of the patient along with the medical devices without detaching and reattaching wires, tubes, cords and interfaces for the medical devices.

In one embodiment, the structure includes a mattress support 118. In this embodiment, the structure includes a mattress 119 positioned on the mattress support 118 to further support the patient. In another embodiment, the system 100 includes bed rails 123 and 124 to secure the patient on the mattress 119, which in some embodiments may be warmed. The bed rails 123 and 124 can be set in an up position to prevent a patient from falling off the mattress 119, or in a down position to allow health care personnel access to the patient. In another embodiment, the structure includes an adjustment mechanism 116-117 for adjusting the position and height of the structure.

In one embodiment, the structure includes a vertical frame 120 to support one or more medical devices. The vertical frame 120 may include lighting elements such as overhead halogen long-lived bulbs 181 as depicted in FIG. 4. In another embodiment, detachable lighting elements appropriate for surgical procedures or hyperbilirubin therapy may be added (not shown). The vertical frame 120 may also include a display 132 with a camera 620 attached to the bottom of the display 132. The camera 620 is discussed below in FIG. 6. In this embodiment, the display 132 is slaved to the computing system 160 and continuously displays selected patient vital signs with a brightness, size, and elevation that can be viewed from a distance. The camera 620 may be used for teleconferencing (with screen 605), remote consultation, visual patient identification/recognition, or transmission of patient images to authorized family members, health providers, or facility administration.

In another embodiment, the structure includes a storage unit 122 mounted on the structure. For example, the storage unit 122 can be a set of drawers for storing medical devices, medical supplies, patient clothing (including diapers) or valuables in a lockable storage container. A tray 138 beneath the mattress 119 has room for an x-ray plate and may be pulled out and reinserted beneath the patient.

In another embodiment, the system 100 includes fluid/air containers 134-135 to record essential patient information (i.e. chest tube output, urine output, and naso-gastric suction output). These fluid/air containers 134-135 are examples of medical monitoring device that are discussed in FIG. 7.

In one embodiment, the structure contains an attachment 163 for suction for air and oxygen as well as portable, regulated canisters of air 137 and oxygen 138.

In another embodiment, the structure includes extra-large wheels 110-113 mounted on the bottom of the structure to facilitate transport of the system 100. In another embodiment, the structure includes a dolly 115 that can support various medical devices and equipment. In some embodiments, the wheels 110-113 are mounted to the bottom of the dolly 115. In some embodiments, the wheels have a locking feature to prevent movement of the system 100.

In one embodiment, the system 100 includes one or more hooks 121 supported by and mounted on the vertical frame 120 and is capable of supporting an intravenous bag 130.

In one embodiment, the system 100 includes an electrical plug (not shown) and twenty to twenty five electrical outlets 150-152 mounted on the structure. The electrical plug connects to a conventional wall outlet for supplying electrical power to the medical devices and the computing system 160 plugged into the electrical outlets 150-152. In another embodiment, the system 100 includes a power supply 155 for supplying power to the computing system 160 and the medical devices. The structure supports the power supply (e.g., battery or electrical generator), which may be mounted on the structure. Additionally, the power supply acts as a backup power source for the computing system 160 and the medical devices when main electrical power is disrupted (e.g., a blackout occurs). In some embodiments, the power supply 155 may act as a heavy counterbalance for the system 100. Also, the power supply 155 may be recharged when the electrical plug is connected to a wall outlet.

In another embodiment, the structure includes a swivel arm 114 to support the keyboard 600 and the display device 605. The keyboard 600 and the display device 605 are discussed in further detail below in FIG. 6. A bar code reader 610 is alongside the keyboard 600. Also, a data read/write device 635 is at the side of the keyboard 600. An identification device 615 such as a biometric device is placed on the keyboard 600. A speaker 625 and a microphone 630 are located on the display device 605. The display device 132 may also have a green light 173 and a red light 174 for the color light system 650. The bar code reader 610, the identification device 615, the speaker 625, the microphone 630, the data read/write device 635, and the color light system 650 are discussed in further detail below in FIG. 6.

In a further embodiment, the keyboard 600 and the display device 605 can be mounted on the swivel arm 114. The swivel arm 114 allows health care personnel or the patient to position the keyboard 600 and the display device 605 for convenient access to the computing system 160. In some embodiments, the structure has mounts 180 on either side in order to fit into patient space of variable dimension and limitation.

Various components in the system 100 can be arranged in an ergonomic fashion both for the patient and the health care personnel. In one example for the patient, the mattress 119 is soft and positioned such that the patient may be rolled into different positions. In one example for the health care personnel, the keyboard 600 and the display device 605 are arranged to prevent repetitive use syndromes (i.e. carpal-tunnel) and eye or back strains. In addition, in some embodiments, the system 100 is designed to be easily cleaned for possible sterilization and storage. In some embodiments, the material used for the system 100 should be durable for intensive use, frequent transport, cleaning with astringent liquids, and support for heavy equipment. In some embodiments, the material used for the system 100 should be also impermeable to a patient's bodily fluids such as urine, stool, saliva, and blood. In some embodiments, the components within the system 100 are color-coded to safely assist health care personnel in identifying and correctly placing the components. In some embodiments, the components within the system 100 are modular such that the different components can be easily detached from the system 100 to allow for transfer and maintenance.

Figure 5:
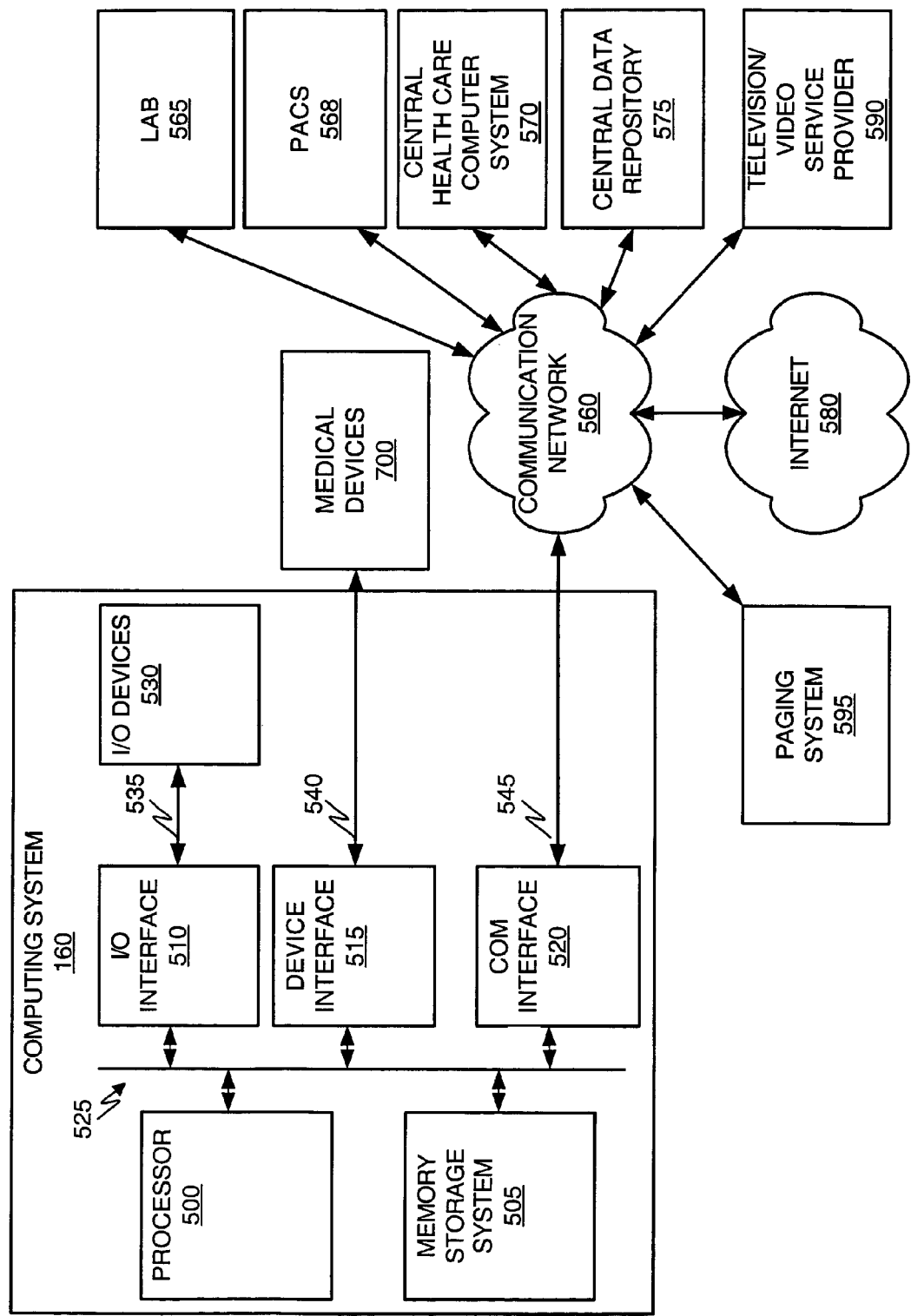
FIG. 5 is a diagram of an exemplary computing system, medical devices, and a communication network in an exemplary implementation of the present invention.

FIG. 5 depicts a diagram of the computing system 160, medical devices 700, a communication network 560, a central facility computer system 570, the Internet 580, a television/video service provider 590, and a paging system 595 in an exemplary implementation of the invention. The computing system 160 includes a processor 500, a memory storage system 505, an input-output (I/O) interface 510, a device interface 515, and a communication interface 520 that are coupled to each other, and communicate with each other, via a bus 525. The computing system 160 also includes input-output (I/O) devices 530 that are coupled to, and communicate with, the I/O interface 510 through bus 535. In some embodiments, the interconnections, links, or buses between the elements in FIG. 5 can be wired or wireless. Also, in some embodiments, the interconnections, links, or buses between the elements in FIG. 5 can be broadband.

The processor 500 retrieves and executes operating software and application software from the memory storage system 505. The memory storage system 505 stores data and software. The memory storage system 505 could comprise a disk, tape, integrated circuit, server, or some other memory device. The memory storage system 505 may be distributed among multiple memory devices.

The I/O interface 510 exchanges data between the bus 525 and the I/O devices 530 exchange data (e.g., patient information and control instructions). The I/O devices 530 are discussed in further detail below in FIG. 6.

The device interface 515 is coupled to, and communicates with, the medical devices 700 via communications link 540. The medical devices 700 provide data (e.g. status information of the patient) to the device interface 515. In some embodiments, the output of the medical devices is in a digital signal format. The digitization of the medical devices 700 provide easier integration between the medical devices 700 and other components that may interface with the medical devices 700.

The communication interface 520 could comprise a network interface card, modem, port, or some other communication device. The communication interface 520 may be distributed among multiple communication devices. The communication interface 520 is coupled to and communicates with the communication network 560 via communications link 545, as is described more fully herein. For example, the communication network 560 can be a wireless communication network. In one embodiment, the communication network 560 is coupled to and communicates with a central facility computer system 570, which may have functions that include but are not limited to: billing, human resource management, personalized health provider data sets, coding, maintenance, medical and pharmacy rules, insurance, and administrative functionality. The central data repository (CDR) 575 is coupled to the communication network 560. In one embodiment, the central facility computer system 570 includes the central data repository 575 of patient medical records (e.g., electronic medical records) and can store the data received from the communication interface 520 into the CDR 575. Further, in this embodiment, the communication interface 520 can access data (e.g., medical records, patient information, status information, or control instructions) in the CDR 575 or the central facility computer system 570. For example, the computing system 160 can access and/or automatically download appropriate electronic images (e.g., PACS) from the database of medical records and display the images on an I/O device 530 (e.g. display 605) or store the images in the memory storage system 505 for subsequent access. The storage of data into both the computing system 160 and the database provides data reliability and data redundancy. Additionally, the availability of patient information at a patient's bedside allows time-efficient review of patient data, confirmation of review visitation, and enhanced decision support. It also allows bedside paging through the paging system 595 for selective or automated notification of medical personnel.

In one embodiment, the communication interface 520 can exchange data with the lab 565 and the patient archiving system 568 (PACS) via the communication network 560. In one embodiment, the communication interface 520 can exchange data with the Internet 580 via the communication network 560. In another embodiment, the communication interface 520 can access data (e.g., a television broadcast) from a cable television/video service provider 590 via the communication network 560. In still another embodiment, the communication interface 520 can access data (e.g. movies or sound tracks) from a central facility computer system 570 via the communication network 560.

Figure 6:
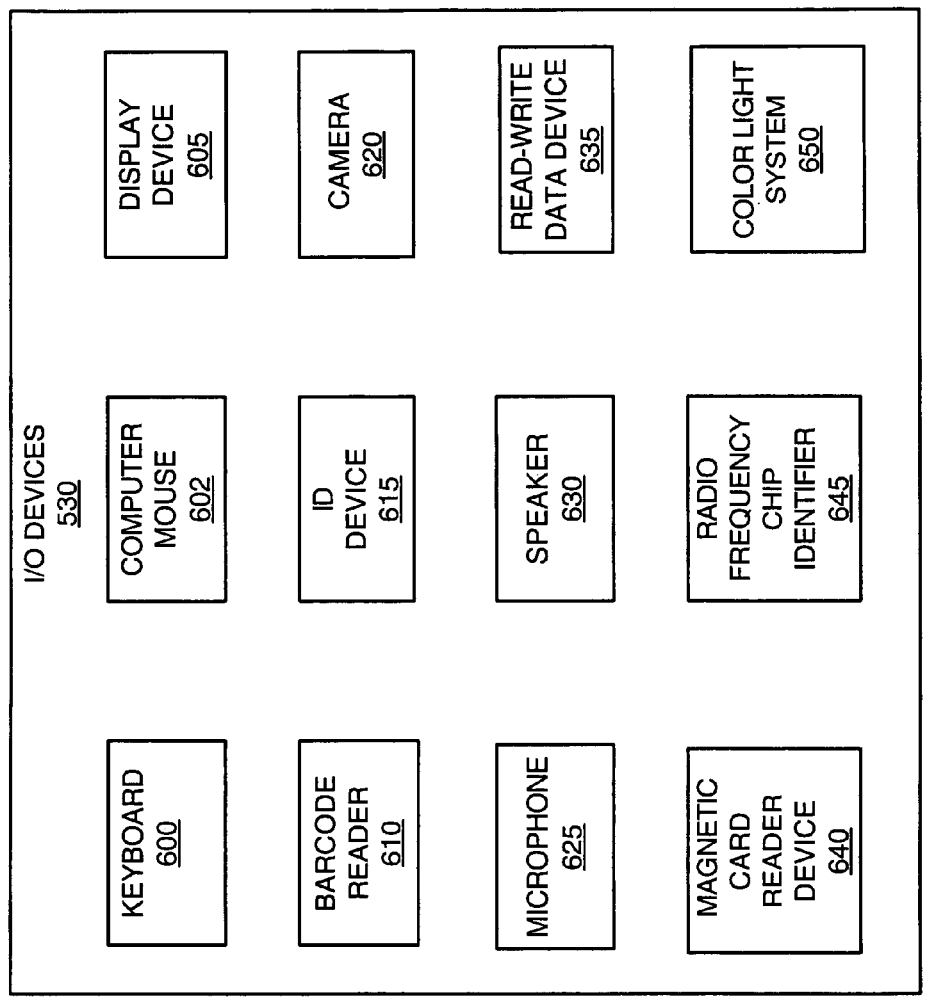
FIG. 6 is a block diagram of exemplary input-output devices in an exemplary implementation of the present invention.

FIG. 6 depicts a block diagram of the I/O devices 530 in an exemplary implementation of the invention. The exemplary I/O devices 530 include a keyboard 600, a computer mouse 602, a display device 605, a bar code reader 610, an identification (ID) device 615, a camera 620, a microphone 625, a speaker 630, a read-write data device 635, a magnetic card reader 640, a radio frequency chip identifier 645, and a color light system 650, which are each coupled to, and communicate with the I/O interface 510 (FIG. 5). The keyboard 600 and computer mouse 602 allows a person (e.g., health care personnel) to enter data (e.g., patient information or control instructions) into the computing system 160. In some embodiments, the computer mouse 602 operates together with the display device 605 to allow a user to control a graphical user interface (FIG. 9) for the computing system 160.

The display device 605 receives data (e.g., patient information, device output, or control instructions) from the I/O interface 510 and generates a visual display based on the data. In one embodiment, the display device 605 is a large (>17 inches) flat-panel touch screen that allows a user to input data (e.g., control instructions, patient orders, and patient information) into the computing system 160. For example, health care personnel could use the display device 605 to monitor the status of an IV bag, including the contents of the IV bag, the concentration of solution in the IV bag, and the rate of administration of the solution in the IV bag. It is to be appreciated that the display device 605 allows for centralized control and monitoring of the medical devices. Additionally, the display device 605 can eliminate the need for individual display devices or control panels for the medical devices.

In one embodiment, the display device 605 can be used by the patient. For example, the display device 605 can display a web browser that allows a patient the surf the Internet. As another example, the display device 605 can receive a cable television program broadcast from the I/O interface 510 and display the cable television broadcast. In another embodiment, the display device 605 receives data (e.g., DVD movie data or medical educational videos specific to the patient's circumstances) from the I/O interface 510 and displays the data as a video stream (e.g., a movie). In this embodiment, the computing system 160 provides entertainment to the patient via the display device 605. In one embodiment, the computing system 160 includes a TIVO-like device (not shown) for recording and playing back television programs, so that complete program viewing, even when interrupted by medical necessity, may still take place.

In one embodiment, the display device 605 displays a virtual medical chart of a patient and accepts entry of physician's orders via a graphic user interface. In another embodiment, the display device 605 displays a graphical representation of patient information received from the medical devices. In still another embodiment, the display device 605 displays decision-making options for health care personnel generated by the computing system 160 based on medical logic rules and the patient information. In one embodiment, the communication network 560, the ID device 615, and the central facility computer system 570 allow medical personnel to personalize the ways and sequences in which they want data displayed on the display device 605.

Additionally, the bed system may enable application of virtual medical logic and rules analyses to assist patients and physicians in areas of medicine characterized by a rapid expansion of knowledge and research data exceeding the integrative capacity of some busy, practicing clinicians.

The barcode reader 610 reads barcodes, generates data based on the barcodes, and provides the data to the I/O interface 510. For example, a patient or provider may have an identifying wristband barcode. As another example, a medication container, such as an intravenous bag, may have a barcode for identifying the contents of the medical container and characteristics of the contents (e.g., expiration date, dose, and concentration). The wristbands and medication containers can be scanned at approximately the same time to ensure that the proper medication is administered to the correct patient at the appropriate time by the designated person. In this way, the probability of medication error is reduced and the accuracy of the medical record is enhanced.

In one embodiment, the barcode reader 610 reads a barcode on a patient's wristband and determines whether the patient has insurance coverage. In another embodiment, the computing system 160 reads a barcode on medical supplies administered to the patient and applies the charges for the medical supplies to the patient's account.

The identification device 615 generates data based on the physical characteristics of persons and provides the data to the I/O interface 510. Some examples of the identification device 615 are biometric devices such as a fingerprint recognition device, a voice recognition device, and a retinal scanner. These biometric devices enhance the audit trail and advantageously increase security of the computing system 160 to prevent unauthorized users.

In one embodiment, the computing system 160 attempts to identify a person based on the data received from the identification device 615. Once identified, the computing system 160 determines if the person is authorized to operate the computing system 160 and organizes their data display according to predetermined preferences. The computing system 160 can then selectively control access to the computing system 160 and the medical devices based on the identity of the person associated with the data. Additionally, the computing system 160 can record a time and date stamp for each attempted access to the computing system 160—both confirming medical visits and alerting system administrators to attempted visits by unwanted persons (i.e. computer hackers, unauthorized medical personnel, and others). In one embodiment, the computing system 160 requires a password to confirm the identity of the person attempting to access the computing system 160. Identifying the person and controlling access to the computing system 160 increases security to the patient and prevents unauthorized persons (e.g., computer hackers) from accessing the computing system 160.

The camera 620 generates visual images and provides the visual images to the I/O interface 510. In one embodiment, the camera 620 is part of the identification device 615. In this embodiment, the camera 620 generates a visual image of the person attempting to operate the computing system 160. In another embodiment, the camera 620 generates visual images of the patient and transmits the visual images to a remote display device (e.g., a display monitor in another hospital room or family member's home). In this way, a patient's family or friends can view the patient when immediate access to the patient is not possible, or hospital personnel may verify that the bed is empty. Additionally, the camera device 620 enables a patient to teleconference with visitors, business associates, and remote health care providers including consultants.

The microphone 625 allows the entry of sound data into the computing system 160. In one embodiment, the microphone 625 is part of the identification device 615. In this embodiment, the microphone 625 generates sound data based on a user's voice.

In another embodiment, the microphone 625 is used for verbal data entry, such as dictation, or for teleconferencing. Voice recognition technologies, as they mature, will permit greater verbal and less manual provider order entry and charting.

The speaker 630 provides sound to the patient or health care personnel. For example, the speaker 630 can provide music or television audio to the patient. As another example, the speaker 630 can provide an audible sound to alert health care personnel of an event. For example, the speaker 630 can provide an audible sound in response to the arrival of a new x-ray or notification that a medication should be administered. As another example, the speaker 630 can sound an audible alert when the computing system 160 measures aberrant vital signs of the patient. In one embodiment, the speaker 630 and the microphone 625 are located at the top of the display device 605.

The read-write data device 635 allows data (e.g., patient information and entertainment information) to be entered into the computing system 160. Additionally, the read-write data device 635 allows data (e.g., a patient's medical record) to be stored on a memory device. An example of the read-write data device 635 is a Digital Versatile Disk (DVD) read-write drive. The read-write device data 635 may be used to transfer files to or from the memory storage system 505 of the computing system 160, and to create a personal health record for patients at the time of discharge. The read-write data device 635 may also be used to watch medically oriented, educational, or entertaining video material.

The magnetic card reader 640 reads data in a magnetic strip of an identification card and provides the data to the I/O interface 510. In one embodiment, the computing system 160 uses the data read from the magnetic strip of an identification card to identify a person (e.g., a physician) associated with the identification card. The computing system 160 can then control access to the computing system 160 and the medical devices based on the identity of the person associated with the identification card.

The radio frequency chip identifier 645 allows wireless confirmation of identities by the system 100. This includes the identity of the patient, visitors, health care providers, and devices currently in use for patient care.

The color light system 650 includes lights for indicating whether there are abnormal patient results in need of health provider attention. The display device 132 may also have a green light 173 and a red light 174 for the color light system 650.

In some embodiments, the system 100 provides consumer electronics for the patient's entertainment, education, or medical research. For example, the patient can watch a movie using the DVD drive and the computing system 160. The patient can also perform web surfing and e-mail over the Internet 580 using the computing system 160. The patient may also use the computing system 160 for video games. In another example of use of consumer electronics, the camera 620 can take pictures of an infant for posting on a website or transmission to family and friends.

FIG. 7 depicts a block diagram of medical devices 700 in an exemplary implementation of the invention. The medical devices 700 include medical care devices 710 and medical monitoring devices 730. The medical care devices 700 provide medical care to a patient. The medical monitoring devices 730 measure the physiological status of the patient.

The medical care devices 710 include a ventilator 170, intravenous pumps 136, a radiant heater 131, a defibrillator 718, and a food pump 720. The ventilator 170 controls the respiration of a patient based on data (e.g., control instructions) received from the device interface 515 (FIG. 5). The intravenous pumps 136 deliver solutions containing a medication into a patient's bloodstream under pressure at a regulated flow rate based on data (e.g., control instructions) received from the device interface 515. The radiant heater 131 warms the patient to a desired temperature. The defibrillator 718 delivers cardioverting or defibrillating energy to the patient according to the facility-defined protocols and user authorization. The food pump 720 delivers liquid nutrition to the patient's gastrointestinal tract.

The exemplary medical monitoring devices 730 include an oxygen monitor 732, a carbon dioxide monitor 734, a glucose monitor 736, a temperature monitor 738, an invasive blood pressure monitor 740, a non-invasive blood pressure monitor 742, a heart monitor (e.g. EKG) 744, a weight monitor 746, a central venous pressure (CVP) monitor 748, a respiration monitor 750, a pulse monitor 752, fluid/air output monitor 134-135, a cerebrospinal fluid (CSF) pressure monitor 756, and a tissue compartment pressure monitor 758. The fluid/air output monitors 134-135 are configured to monitor output of air and body fluids such as urine, nasogastric suction, chest tube output, biliary secretions, abdominal drain output, or other fluids. The weight monitor 746 is used to verify weight-based dosing to prevent a wrong dosage of medication for a specific weight. The CSF pressure monitor 756 is attached to an intracranial or intraspinal pressure monitoring device. The tissue compartment pressure monitor 758 is attached to a probe or transduced tube (gastric tube, bladder catheter) to follow the intracompartmental pressure of various body cavities.

FIG. 8 depicts an exemplary method of operating the system 100 (FIG. 1) in an exemplary implementation of the invention. FIG. 8 begins in step 800. In step 802, the structure supports a patient, the computing system 160, and one or more medical devices 700. The medical devices 700 supported by the structure can be medical care devices 710 or medical monitoring devices 730 (FIG. 7).

In step 804, the computing system 160 identifies a person attempting to operate the computing system 160. In one embodiment, that person enters a code into the computing system 160 or the barcode reader 610 reads data in a barcode associated with the person for identifying the person. In another embodiment, the identification device 615 uses biometric characteristics to identify the person. In another embodiment, the magnetic card reader 640 reads data in a magnetic strip of an identification card for identifying the person. In yet another embodiment, the person carries a radio frequency chip which is wirelessly used to record their presence.

Also in step 804, the computing system 160 controls access to the computing system 160 and the medical devices 700 based on the identity of the person attempting to operate the computing system 160. Identification of persons attempting to operate the computing system 160 provides a level of security to the patient and allows the computing system 160 to track the persons operating the computing system 160.

In step 806, the computing system 160 identifies the patient. In one embodiment, the barcode reader 610 reads data in a barcode imprinted on a wristband worn by the patient and the computing system 160 identifies the patient based on the data. In another embodiment, the ID device 615 may recognize a biometric signature (e.g. fingerprint or retinal scan) or radio frequency tag. In one embodiment, the computing system 160 provides the data to a health care computer system for retrieval and later storage in a database containing patient medical records.

In step 808, the computing system 160 identifies a medication to be administered to the patient. In one embodiment, the barcode reader 610 reads data in a barcode imprinted on a container containing the medication. The computing system 160 then identifies the medication based on the data. The computing system 160 may then use its own integrated database complete with hospital pharmacy and lab protocols to determine medication allergies, interactions, and drug dosing, generating alerts when appropriate.

In step 810, the computing system 160 controls the medical care devices 710 to provide medical care to the patient. In this process, the computing system 160 provides control instructions to the medical care devices 710 (FIG. 7) to control the operation of the medical care devices 710. For example, a physician can enter data (e.g., control instructions) into the computing system 160 via the keyboard 600, and the computing system 160 can provide the data to the medical care devices 710.

In step 812, the computing system 160 receives data for a patient (e.g., physiological status information) from the medical devices 700 and a remote computing system such as the central facility computer system 570. For example, the data received from the medical devices 700 can include the vital signs of the patient. In one embodiment, the computing system 160 receives the data from one or more medical monitoring devices 730.

In step 814, the computing system 105 displays data (e.g., patient information, control instructions, status information) on the display device 605. In one embodiment, the computing system 160 includes a graphical user interface (GUI) for displaying the data, as is described more fully herein. In step 816, the computing system 160 accepts instructions, prescriptions, and servations identification.

In step 818, the computing system 160 provides data (e.g., patient information, control instructions, status information) to a health care computer system via a communication network. In this embodiment, the computing system 160 can access data (e.g., patient information, control instructions, status information) from the health care computer system via the communication network.

In step 820, the system 100 is transported to a different location. In this process, the patient, the computing system 160, and the medical devices 700 are transported together by the structure as a single unit to a different location. In one embodiment, the Power supply supplies power to the computing system 160 and the medical devices 700 during transport.

FIG. 9 depicts an exemplary screen shot 900 of a display generated by the graphical user interface. As shown in FIG. 9, the display includes a representation of status information (e.g., vital signs of a patient) and control instructions (e.g., ventilator data and intravenous pump data). Additionally, the display includes various control points for operating the computing system 160. In one embodiment, the GUI in FIG. 9 can be operated by a touch screen flat panel monitor, the keyboard 600, and/or the computer mouse 602.

The above-described elements can be comprised of instructions that are stored on storage media. The instructions can be retrieved and executed by a processor. Some examples of instructions are software, program code, and firmware. Some examples of storage media are memory devices, tape, disks, integrated circuits, and servers. The instructions are operational when executed by the processor to direct the processor to operate in accord with the invention. Those skilled in the art are familiar with instructions, processor, and storage media.

Those skilled in the art will appreciate variations of the above-described embodiments that fall within the scope of the invention. As a result, the invention is not limited to the specific examples and illustrations discussed above, but only by the following claims and their equivalents.

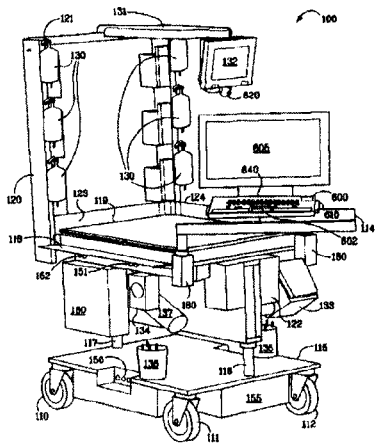

What is claimed is:

1. An integrated point-of-care system comprising:
 a single integrated device for providing integrated point-of-care, the single integrated device including:
  a bed structure configured as a part of the single integrated device and including a mattress and four wheels for supporting the entire body of a patient, the bed structure having a mattress positioned on a support structure for supporting the entire body of the patient;
  one or more medical monitoring devices configured as a part of the single integrated device and configured to monitor patient information for a patient;

one or more a medical care devices configured to provide medical care to the patient; and an interactive computing system configured as a part of the single integrated device and configured to receive patient information from the medical monitoring devices, transmit the patient information to a central data repository, interpret the patient information and display the patient information on a display device for health care providers and administrative personnel, transmit control instructions to the medical care devices located with the patient on the structure based on the patient information, generate decision-options for providers based on medical logic rules including artificial intelligence, and display decision support research data to enhance provider decision making, the bed structure integrated within the single integrated device and being a single mobile unit configured to support the patient's weight, the bed structure integrated as part of the single device with the mattress, the medical monitoring devices, the medical care devices, and the interactive computing system that receives, transmits, interprets, and displays information about the patient and controlling the devices which provide care to the patient.

2. The integrated point-of-care system of claim 1 wherein the patient information comprises vital signs of the patient.

3. The integrated point-of-care system of claim 1 wherein the structure comprises a bed mattress and frame configured to support the patient.

4. The integrated point-of-care system of claim 1 wherein the medical care device is configured to administer a medication to the patient.

5. The integrated point-of-care system of claim 1, the single integrated device further comprising a power supply configured to supply power to the medical care device and the medical monitoring device.

6. The integrated point-of-care system of claim 5 wherein the power supply comprises a battery.

7. The integrated point-of-care system of claim 1 wherein the computing system further comprises a display device configured to display the control instructions or patient information.

8. The integrated point-of-care system of claim 7, wherein the display device comprises a flat-screen touch panel configured to allow user input for controlling the operation of the medical care device or the medical monitoring device, the display device having a screen size of at least seventeen inches in length.

9. The integrated point-of-care system of claim 1 wherein the computing system further comprises a keyboard.

10. The integrated point-of-care system of claim 1 wherein the communication network is wireless.

11. The integrated point-of-care system of claim 1 wherein the computing system further comprises a memory storage system configured to store the patient information or control instructions.

12. The integrated point-of-care system of claim 1 wherein the computing system further comprises an identification device configured to identify a person.

13. The integrated point-of-care system of claim 12, wherein the identification device comprises a fingerprint recognition device.

14. The integrated point-of-care system of claim 12, wherein the identification device comprises a voice recognition device.

15. The integrated point-of-care system of claim 12, wherein the identification device comprises a visual recognition device.

16. The integrated point-of-care system of claim 1 further comprising a camera configured to generate a visual image.

17. The integrated point-of-care system of claim 1 wherein the computing system further comprises a barcode reader.

18. The integrated point-of-care system of claim 1 wherein the computing system further comprises a communication interface configured to communicate with the Internet.

19. The integrated point-of-care system of claim 1 wherein the computing system further comprises a communication interface configured to communicate with a television service provider.

20. The integrated point-of-care system of claim 1 further comprising a plurality of wheels mounted on the bottom of the structure to facilitate transport of the patient and the medical devices.

21. The integrated point-of-care system of claim 1 further comprising a radiant warming device mounted on the structure to warm the patient.

22. A method of operating an integrated point-of-care system comprising the steps of:

supporting the entire body of a patient with a single integrated device, the single integrated device comprising a bed structure, a computing system, medical care device, and medical monitoring device, the single integrated device configured to allow the integrated point of care system to operate as a mobile point of care device as a single unit;

receiving patient information from the medical monitoring device into the computing system;

interpreting the received patient information;

accepting control instructions from a provider, the instructions to be transmitted to the medical care device through the computing system to provide medical care to the patient based on the patient information;

transmitting control instructions to medical devices;

applying virtual medical logic based on patient information and research data to generate diagnostic and therapeutic options for providers based on medical logic, providing the decision-making options for display;

executing the therapeutic options;

exchanging data between the computing system and a central data repository through a communication network; and transporting the patient, the medical monitoring device, the medical care device, and the computing system together using the single integrated device.

23. The method of claim 22 further comprising the step of displaying the patient information.

24. The method of claim 22, further comprising the step of identifying a person authorized to operate the computing system by using an identification device.

25. The method of claim 22, further comprising the step of identifying the patient by using an identification device.

26. The method of claim 22, further comprising the step of identifying a medication to be administered to the patient by using an identification device.

* * * * *

UNITED STATES PATENT AND TRADEMARK OFFICE
CERTIFICATE OF CORRECTION

| | | |
|---|---|---|
| PATENT NO. | : 8,005,686 B2 | Page 1 of 2 |
| APPLICATION NO. | : 10/825729 | |
| DATED | : August 23, 2011 | |
| INVENTOR(S) | : Mallory | |

It is certified that error appears in the above-identified patent and that said Letters Patent is hereby corrected as shown below:

On the title page item (12) delete "Smith" and insert --Mallory--

Item (76) delete "Baird, M. Smith" and insert --Baird M. Mallory-- as shown on the attached title page Signed and Sealed this
Seventeenth Day of January, 2012

David J. Kappos
*Director of the United States Patent and Trademark Office*

(12) United States Patent
Mallory

(10) Patent No.: US 8,005,686 B2
(45) Date of Patent: Aug. 23, 2011

(54) INTEGRATED POINT-OF-CARE SYSTEMS AND METHODS

(76) Inventor: Baird M. Mallory, Monte Sereno, CA (US)

(*) Notice: Subject to any disclaimer, the term of this patent is extended or adjusted under 35 U.S.C. 154(b) by 1307 days.

(21) Appl. No.: 10/825,729

(22) Filed: Apr. 16, 2004

(65) Prior Publication Data
US 2004/0249673 A1  Dec. 9, 2004

Related U.S. Application Data

(60) Provisional application No. 60/463,999, filed on Apr. 18, 2003.

(51) Int. Cl.
*G06Q 10/00* (2006.01)
(52) U.S. Cl. .................................. 705/2; 705/3
(58) Field of Classification Search .............. 705/2, 3
See application file for complete search history.

(56) References Cited

U.S. PATENT DOCUMENTS

| | | | |
|---|---|---|---|
| 4,347,851 A | 9/1982 | Jundanian | |
| 4,633,237 A | 12/1986 | Tucknott et al. | |
| 4,768,241 A | 9/1988 | Beney | |
| 4,803,625 A | 2/1989 | Fu et al. | |
| 5,253,656 A | 10/1993 | Rincoe et al. | |
| 5,335,651 A | 8/1994 | Foster et al. | |
| 5,343,869 A | 9/1994 | Pross et al. | |
| 5,417,222 A | 5/1995 | Dempsey et al. | |
| 5,455,975 A | 10/1995 | Foster | |
| 5,497,766 A | 3/1996 | Foster et al. | |
| 5,664,270 A | 9/1997 | Bell et al. | |
| 5,678,562 A | 10/1997 | Sellers | |
| 5,687,717 A | 11/1997 | Halpern et al. | |
| 5,749,374 A | 5/1998 | Schneider, Sr. | |
| 5,993,400 A | 11/1999 | Rincoe et al. | |
| 6,017,307 A | 1/2000 | Raines | |
| 6,111,509 A | 8/2000 | Holmes | |
| 6,139,494 A * | 10/2000 | Cairnes | 600/300 |
| 6,149,587 A | 11/2000 | Raines | |
| 6,162,180 A | 12/2000 | Miesel et al. | |
| 6,168,563 B1 | 1/2001 | Brown | |
| 6,171,237 B1 | 1/2001 | Avitall et al. | |
| 6,205,601 B1 * | 3/2001 | Nessmann et al. | 5/600 |
| 6,206,837 B1 | 3/2001 | Brugnoli | |
| 6,234,172 B1 | 5/2001 | Ausbourne et al. | |
| 6,264,614 B1 | 7/2001 | Albert et al. | |
| 6,360,389 B1 | 3/2002 | Gallant et al. | |
| 6,362,725 B1 | 3/2002 | Ulrich et al. | |

(Continued)

OTHER PUBLICATIONS

"'Smart' Hospital to Improve Care," BBCNews, May 7, 2003, located at http://news.bbc.co.uk/2/hi/technology/3004089.stm.

(Continued)

*Primary Examiner* — Lena Najarian
(74) *Attorney, Agent, or Firm* — Carr & Ferrell LLP

(57) ABSTRACT

An integrated point-of-care system includes a medical monitoring device, a medical care device, a computing system, and a structure. The medical monitoring device monitors patient information for a patient. The medical care device provides medical care to the patient. The computing system receives patient information from the medical monitoring device and transmits control instructions to the medical care device to control the medical care to the patient. The computing system also exchanges data with a central data respository through a communication network. The structure supports the patient, the medical monitoring device, the medical care device, and the computing system. The structure can also transport the patient, the medical monitoring device, the medical care device, and the computing system together.

26 Claims, 9 Drawing Sheets

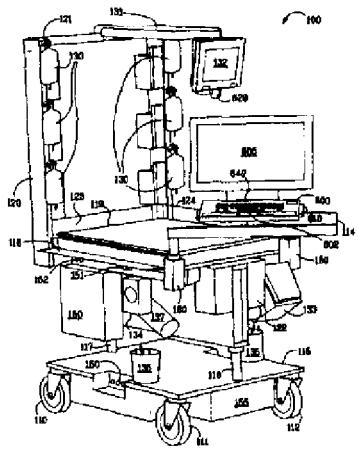

UNITED STATES PATENT AND TRADEMARK OFFICE
CERTIFICATE OF CORRECTION

| | |
|---|---|
| PATENT NO. | : 8,005,686 B2 |
| APPLICATION NO. | : 10/825729 |
| DATED | : August 23, 2011 |
| INVENTOR(S) | : Mallory |

It is certified that error appears in the above-identified patent and that said Letters Patent is hereby corrected as shown below:

On the title page item (12) delete "Smith" and insert --Mallory--

Item (76) delete "Baird M. Smith" and insert --Baird Mallory-- as shown on the attached title page This certificate supersedes the Certificate of Correction issued January 17, 2012.

Signed and Sealed this
Twenty-second Day of May, 2012

David J. Kappos
*Director of the United States Patent and Trademark Office*

(12) United States Patent
Mallory

(10) Patent No.: US 8,005,686 B2
(45) Date of Patent: Aug. 23, 2011

(54) INTEGRATED POINT-OF-CARE SYSTEMS AND METHODS

(76) Inventor: Baird Mallory, Monte Sereno, CA (US)

( * ) Notice: Subject to any disclaimer, the term of this patent is extended or adjusted under 35 U.S.C. 154(b) by 1307 days.

(21) Appl. No.: 10/825,729

(22) Filed: Apr. 16, 2004

(65) Prior Publication Data

US 2004/0249673 A1   Dec. 9, 2004

Related U.S. Application Data

(60) Provisional application No. 60/463,999, filed on Apr. 18, 2003.

(51) Int. Cl.
   *G06Q 10/00* (2006.01)
(52) U.S. Cl. .................................. 705/2; 705/3
(58) Field of Classification Search ............... 705/2, 3
   See application file for complete search history.

(56) References Cited

U.S. PATENT DOCUMENTS

| | | |
|---|---|---|
| 4,347,851 A | 9/1982 | Jundanian |
| 4,633,237 A | 12/1986 | Tucknott et al. |
| 4,768,241 A | 9/1988 | Beney |
| 4,803,625 A | 2/1989 | Fu et al. |
| 5,253,656 A | 10/1993 | Rincoe et al. |
| 5,335,651 A | 8/1994 | Foster et al. |
| 5,343,869 A | 9/1994 | Pross et al. |
| 5,417,222 A | 5/1995 | Dempsey et al. |
| 5,455,975 A | 10/1995 | Foster |
| 5,497,766 A | 3/1996 | Foster et al. |
| 5,664,270 A | 9/1997 | Bell et al. |
| 5,678,562 A | 10/1997 | Sellers |
| 5,687,717 A | 11/1997 | Halpern et al. |
| 5,749,374 A | 5/1998 | Schneider, Sr. |
| 5,993,400 A | 11/1999 | Rincoe et al. |
| 6,017,307 A | 1/2000 | Raines |
| 6,111,509 A | 8/2000 | Holmes |
| 6,139,494 A * | 10/2000 | Cairnes ............... 600/300 |
| 6,149,587 A | 11/2000 | Raines |
| 6,162,180 A | 12/2000 | Miesel et al. |
| 6,168,563 B1 | 1/2001 | Brown |
| 6,171,237 B1 | 1/2001 | Avitall et al. |
| 6,205,601 B1 * | 3/2001 | Nessmann et al. ............. 5/600 |
| 6,206,837 B1 | 3/2001 | Brugnoli |
| 6,234,172 B1 | 5/2001 | Ausbourne et al. |
| 6,264,614 B1 | 7/2001 | Albert et al. |
| 6,360,389 B1 | 3/2002 | Gallant et al. |
| 6,362,725 B1 | 3/2002 | Ulrich et al. |

(Continued)

OTHER PUBLICATIONS

"'Smart' Hospital to Improve Care," BBCNews, May 7, 2003, located at http://news.bbc.co.uk/2/hi/technology/3004089.stm.

(Continued)

*Primary Examiner* — Lena Najarian
(74) *Attorney, Agent, or Firm* — Carr & Ferrell LLP

(57) ABSTRACT

An integrated point-of-care system includes a medical monitoring device, a medical care device, a computing system, and a structure. The medical monitoring device monitors patient information for a patient. The medical care device provides medical care to the patient. The computing system receives patient information from the medical monitoring device and transmits control instructions to the medical care device to control the medical care to the patient. The computing system also exchanges data with a central data respository through a communication network. The structure supports the patient, the medical monitoring device, the medical care device, and the computing system. The structure can also transport the patient, the medical monitoring device, the medical care device, and the computing system together.

26 Claims, 9 Drawing Sheets